United States Patent [19]

Teach

[11] 4,453,968
[45] Jun. 12, 1984

[54] 3-PERHALOALKYLHYDROXY-OXAZOLIDINES AND THIAZOLIDINES HERBICIDAL ANTIDOTES

[75] Inventor: Eugene G. Teach, El Cerrito, Calif.

[73] Assignee: Stauffer Chemical Company, Westport, Conn.

[21] Appl. No.: 401,486

[22] Filed: Jul. 26, 1982

Related U.S. Application Data

[62] Division of Ser. No. 191,218, Sep. 26, 1980, Pat. No. 4,354,867, which is a division of Ser. No. 077,889, Sep. 21, 1979, Pat. No. 4,259,500.

[51] Int. Cl.$^3$ .................................... A01N 25/32
[52] U.S. Cl. .................................... 71/90; 71/88; 71/100
[58] Field of Search .................. 71/90, 100, 88

[56] References Cited

U.S. PATENT DOCUMENTS

| | | | |
|---|---|---|---|
| 2,571,985 | 10/1951 | Carnes | 260/307 |
| 3,131,509 | 5/1964 | Hoffmann | 47/1 |
| 3,937,716 | 2/1976 | Lewis et al. | 260/307 |
| 3,959,304 | 5/1976 | Teach | 260/307 |

FOREIGN PATENT DOCUMENTS 46-9277  9/1971  Japan .

OTHER PUBLICATIONS

Chemistry and Action of Herbicide Antidotes, Edited by Pallos et al., Academic Press, New York, (1978), p. 10.

Primary Examiner—Catherine L. Mills
Attorney, Agent, or Firm—Harry A. Pacini

[57] ABSTRACT

Compounds having the formula

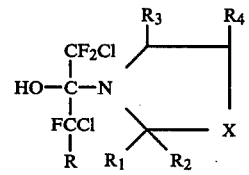

in which
R is selected from the group consisting of chloro and fluoro;
$R_1$–$R_4$ are each independently selected from the group consisting of hydrogen and 1–4 carbon alkyl; and
X is oxygen or sulfur protect crops from thiocarbamate herbicidal injury.

5 Claims, No Drawings

3-PERHALOALKYLHYDROXY-OXAZOLIDINES AND THIAZOLIDINES HERBICIDAL ANTIDOTES

This application is a division of U.S. Ser. No. 191,218, filed Sept. 26, 1980, now U.S. Pat. No. 4,354,867, which in turn is a division of U.S. Ser. No. 077,889, filed Sept. 21, 1979, now U.S. Pat. No. 4,259,500.

BACKGROUND OF THE INVENTION

Uses of Herbicides

An herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate weed pests. They have gained a high degree of commercial success because it has been shown that such control can increase crop yield and reduce harvesting costs.

Herbicidal effectivenss is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the target weed. Certain herbicidal compounds are phytotoxic to some weed species but not to others.

The manufacturer of the herbicide recommends a range of rates and concentrations calculated to maximize weed control. The range of rates varies from approximately 0.01 to 50 pounds per acre (0.0112 to 56 kilograms per hectare (k/ha)), usually from 0.1 to 25 pounds per acre (0.112 to 28 k/ha). The actual amount used depends upon several considerations, including particular weed susceptibility and overall cost limitations.

Need for Herbicidal Antidotes

Unfortunately, few herbicides are selective exclusively of weed species. Many are toxic to both weeds and the intended crop beneficiary. Therefore, a particular herbicide's use may be proscribed by its injurious effect on the cultivated crop even though it may otherwise provide excellent control of weeds plaguing that crop.

To preserve the beneficial aspects of herbicide use and to mitigate crop damage, many herbicidal antidotes have been prepared. These antidotes reduce or eliminate damage to the crop without substantially impairing the ameliorative effect of the herbicide. See U.S. Pat. Nos. 4,021,224 and 4,021,229 and Belgian Pat. No. 846,894.

Although several explanatory theories have been advanced, the precise mechanism by which an antidote reduces herbicidal crop injury while retaining weed injury has not been conclusively established. An antidote compound may in fact be a remedy, interferent, protectant, or antagonist. As used herein, "antidote" describes the effect of establishing herbicidal selectivity.

Thiocarbamate herbicides are particularly effective in the control of grassy type weeds which interfere with the cultivation of a wide variety of crops, e.g., barley, corn, lentils, peanuts, peas, potatoes, soybeans, spinach, tobacco and tomatoes. Frequently, their beneficial use requires the addition of an antidotal compound.

DESCRIPTION OF THE INVENTION

It has been discovered that 3-perhaloalkylhydroxyoxazolidine and thiazolidine compounds are effective antidotes for the projection of a variety of crops from thiocarbamate herbicidal injuries. Such compounds have the following formula

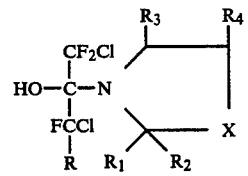

in which

R is selected from the group consisting of chloro and fluoro;

$R_1$–$R_4$ are each independently selected from the group consisting of hydrogen and 1–4 carbon alkyl, preferably methyl or ethyl; and X is oxygen or sulfur.

This invention also includes a two-part herbicidal system comprised of (a) an antidotally effective amount of a compound of the formula

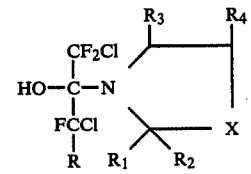

in which

R is selected from the group consisting of chloro and fluoro;

$R_1$–$R_4$ are each independently selected from the group consisting of hydrogen and 1–4 carbon alkyl, preferably methyl or ethyl; and X is oxygen or sulfur; and (b) an herbicidally effective amount of a thiocarbamate of the formula

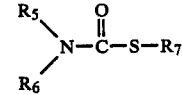

in which $R_5$ is selected from the group consisting of 1–6 carbon alkyl and 2–6 carbon alkenyl;

$R_6$ is selected from the group consisting of 1–6 carbon alkyl, 2–6 carbon alkenyl, cyclohexyl and phenyl; or $R_5$ and $R_6$ together form a 5–10 carbon alkylene ring; and $R_7$ is selected from the group consisting of 1–6 carbon alkyl, 1–4 carbon haloalkyl, 5–10 carbon alkylene ring, phenyl, substituted phenyl, wherein the substituents are 1–4 carbon alkyl, 1–4 carbon haloalkyl, and halo, benzyl, and substituted benzyl, wherein the substituents are 1–4 carbon alkyl, 1–4 carbon haloalkyl, and halo.

The terms "alkyl" and "alkenyl" as used herein are intended to include both straight- and branched-chain groups. The term "halo" is intended to include mono- and polyhalogenated groups. All carbon atom ranges are intended to be inclusive of both upper and lower limits.

This invention also includes the method of protecting crops from herbicidal injury which comprises applying to the locus where protection is desired an antidotally effective amount of a compound of the formula

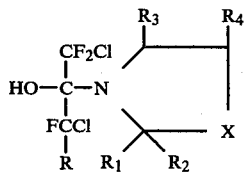

in which

R is selected from the group consisting of chloro and fluoro;

$R_1$–$R_4$ are each independently selected from the group consisting of hydrogen and 1–4 carbon alkyl, preferably methyl or ethyl; and X is oxygen or sulfur.

PREPARATION

The thiocarbamates of the present compositions can be prepared by the procedures described in U.S. Pat. No. 2,913,327.

The oxazolidine and thiazolidine intermediates can be prepared by the methods described by Bergman, et al., 75 Journal of American Chemical Society 358 (1953) and U.S. Pat. No. 3,959,304. The 3-perhaloalkyl oxazolidines are hemiaminals which may be prepared by the reaction of the selected oxazolidine with the appropriate perhaloketone in an inert solvent.

EXAMPLE 1

(Compound No. 4)

Preparation of 2-ethyl-3(1',3'-dichloro-1',1',3',3'-tetrafluoro-2'-hydroxyisopropyl)1,3-oxazolidine Twelve milliliters (ml) of a solution of 2-ethyl-1,3-oxazolidine (4 ml=1 gram (g)) in benzene was added to 25 ml of methylene chloride. To this solution 6 g of 1,3-dichloro-1,1,3,3-tetrafluoroacetone was added dropwise with stirring. After stirring for a few minutes at room temperature, the solution was stripped at reduced pressure, yielding 9.4 g of 2-ethyl-3(1',3'-dichloro-1',1',3',3'-tetrafluoro-2'-hydroxyisopropyl)1,3-oxazolidine ($n_D^{30}$ 1.4640).

EXAMPLE 2

(Compound No. 8)

Preparation of 2,2-dimethyl-3(1',1',3'-trichloro-1',3',3'-trifluoro-2'-hydroxyisopropyl)1,3-thiazolidine Twelve ml of a solution of 2,2-dimethyl-1,3-thiazolidine in benzene (4 ml=1 g) was added to 25 ml of methylene chloride. To this solution, 5.4 g of 1,1,3-trichloro-1,3,3-trifluoroacetone was added dropwise with stirring. After stirring at room temperature for a few minutes, the solution was stripped under reduced pressure, yielding 8.8 g of 2,2-dimethyl-3(1',1',3'-trichloro-1',3',3'-trifluoro-2-hydroxyisopropyl)1,3-thiazolidine ($n_D^{30}$ 1.5022).

EXAMPLE 3

(Compound No. 10)

Preparation of 2,2-dimethyl-3(1',1',3'-trichloro-1',3',3'-trifluoro-2'-hydroxyisopropyl)-4-ethyl oxazolidine Thirteen milliliters (ml) of a solution of 2,2-dimethyl-4-ethyl-1,3-oxazolidine in benzene (4 ml=1 g) was added to 25 ml of methylene chloride. To this solution, 5.4 g of 1,1,3-trichloro-1,3,3-trifluoroacetone was added dropwise with stirring. After stirring at room temperature for a few minutes, the solution was stripped at reduced pressure, yielding 9.3 g of 2,2,-dimethyl-3(1',1',3'-trichloro-1',3',3'-trifluoro-2'-hydroxyisopropyl)-4-ethyl oxazolidine ($n_D^{30}$ 1.4712).

TABLE I

3-PERHALOALKYLHYDROXY-OXAZOLIDINES AND THIAZOLIDINES

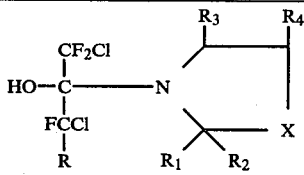

| Compound Number | R | $R_1$ | $R_2$ | $R_3$ | $R_4$ | X | Chemical Name | Physical Constant |
|---|---|---|---|---|---|---|---|---|
| 1 | Cl | CH$_3$ | CH$_3$ | H | H | O | 2,2-dimethyl-3(1',1',3'-trichloro-1',3',3'-trifluoro-2'-hydroxyisopropyl)oxazolidine | $n_D^{30}$ 1.4750 |
| 2 | F | H | H | C$_2$H$_5$ | H | O | 3(1',3'-dichloro-1',1',3',3'-tetrafluoro-2'-hydroxyisopropyl)-4-ethyl oxazolidine | $n_D^{30}$ 1.4542 |
| 3 | Cl | H | H | C$_2$H$_5$ | H | O | 3(1',1',3'-trichloro-1',3',3'-trifluoro-2'-hydroxyisopropyl)-4-ethyl oxazolidine | $n_D^{30}$ 1.4750 |
| 4 | F | H | C$_2$H$_5$ | H | H | O | 2-ethyl-3(1',3'-dichloro- | $n_D^{30}$ 1.4640 |

TABLE I-continued
3-PERHALOALKYLHYDROXY-OXAZOLIDINES AND THIAZOLIDINES

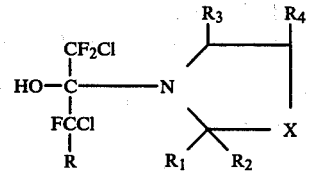

| Compound Number | R | $R_1$ | $R_2$ | $R_3$ | $R_4$ | X | Chemical Name | Physical Constant |
|---|---|---|---|---|---|---|---|---|
| | | | | | | | 1',1',3',3'-tetrafluoro-2'-hydroxyisopropyl) oxazolidine | |
| 5 | F | H | $CH_3$ | $C_2H_5$ | H | O | 2-methyl-3(1',3'-dichloro-1',1',3',3'-tetrafluoro-2'-hydroxyisopropyl)-4-ethyl oxazolidine | $n_D^{30}$ 1.4468 |
| 6 | Cl | H | $CH_3$ | $C_2H_5$ | H | O | 2-methyl-3(1',1',3'-trichloro-1',3',3'-trifluoro-2'-hydroxy-isopropyl)-4-ethyl oxazolidine | $n_D^{30}$ 1.4625 |
| 7 | F | $CH_3$ | $CH_3$ | $C_2H_5$ | H | O | 2,2-dimethyl-3(1',3'-dichloro-1',1',3',3'-tetrafluoro-2'-hydroxyisopropyl)-4-ethyl oxazolidine | $n_D^{30}$ 1.4493 |
| 8 | Cl | $CH_3$ | $CH_3$ | H | H | S | 2,2-dimethyl-3(1',1',3'-trichloro-1',3',3'-trifluoro-2'-hydroxy-isopropyl) thiazolidine | $n_D^{30}$ 1.5022 |
| 9 | Cl | $CH_3$ | $CH_3$ | H | $CH_3$ | O | 2,2,5-trimethyl-3(1',1',3'-trichloro-1',3',3'-trifluoro-2-hydroxyisopropyl) oxazolidine | $n_D^{30}$ 1.4626 |
| 10 | Cl | $CH_3$ | $CH_3$ | $C_2H_5$ | H | O | 2,2-dimethyl-3(1',1',3'-trichloro-1',3',3'-trifluoro-2-hydroxy-isopropyl)-4-ethyl oxazolidine | $n_D^{30}$ 1.4712 |

TESTING

Stock solutions of the herbicides were prepared by diluting the requisite amount of each herbicide in water. The solution compositions and application rates are summarized in Table II.

TABLE II

| | Herbicide Stock Solutions | | | |
|---|---|---|---|---|
| | Composition | | Application | |
| Herbicide Name | Herbicide (mg) | Water (ml) | ml/flat ~ | lb/acre |
| EPTAM ® 6E | 33 | 40 | 4 | 0.50 |
| S—ethyl N,N— dipropyl thio- carbamate | 330 | 40 | 4 | 5.00 |
| | 2240 | 350 | 5 | 6.00 |
| VERNAM ® 6E | 314 | 350 | 5 | 1.00 |
| S—propyl N,N— dipropyl thio- carbamate | 449 | 400 | 5 | 1.25 |
| | 2157 | 400 | 5 | 6.00 |

Stock solutions of each antidote compound were prepared at the desired concentrations by diluting the requisite amounts of each antidote in acetone. The compositions and rates for each method of application are summarized in Table III.

TABLE III

Antidote Stock Solutions
Antidote: 3-Perhaloalkylhydroxy-Oxazolidines and Thiazolidines

| Composition | | Application | | |
|---|---|---|---|---|
| Antidote (mg) | Acetone (ml) | ml/flat | ~ lb/acre | Method* |
| 95 | 15 | 0.30 | 1.00 | IF |
| 95 | 15 | 1.50 | 5.00 | IF |
| 100 | 20 | 1.00 | 1.00 | PPI |
| 100 | 20 | 5.00 | 5.00 | PPI |
| Stock A: | | | | |
| 50 | 100 | | | |
| Dilution: | | | | |
| 10 ml of A | 90 | 4.00 | 0.05 | PPI |
| Seed Treatment: | | | | |
| 500 | 5 | 0.50 ml/ 10 grams seed | 0.5% | ST |

*IF = In-furrow surface application.
PPI = Pre-plant incorporation of herbicide and antidote.
ST = Seed treatment.

All of the soil used in the tests described herein was loamy sand soil treated with 50 parts per million (ppm) each of a commercially available fungicide, N-[tri-chloromethyl)-thio]-4-cyclohexene-1,2-dicarboximide, and 18-18-18 fertilizer, which contains 18% by weight equivalent each of nitrogen, phosphorus pentoxide, and potassium oxide.

The herbicides were applied to the soil by preplant incorporation (PPI). The antidote was applied by PPI, in-furrow, and seed treatment.

For in-furrow (IF) antidote applications, a one pint (473 cubic centimeter) sample of soil from each planting flat was removed and retained. After leveling and furrowing the soil, seeds of the crop or weed species were planted ½ inch deep (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

Seed treatment (ST) consists of shaking in a suitable container 10 g of the seed and 0.5 ml of antidote stock solution.

All flats were placed on greenhouse benches where temperature was maintained between 70° and 90° F. (21.1° to 32.2° C.). The flats were watered by sprinkling as needed to assure good plant growth.

Control flats contained crops treated with herbicides only at the various rates.

Injury ratings were taken four weeks after application of the antidote. The effectiveness of the antidote was determined by visual comparison of injuries to crops and weeds in the control and test flats to those in untreated flats.

The treated crops initially screened for diminution of herbicidal injury were milo, wheat, cotton, rice, barley, corn and soybeans. The herbicides and the most active antidote compositions were then screened on one or two weed species. The weed species tested for control included watergrass (*Echinochloa crusgalli*), foxtail (*Setaria viridis*), and wild oat (*Avena fatua*).

KEY TO TABLES IV AND V

Antidotes

Compound numbers in these tables correspond to the numbers and their chemical description in Table I.

Application:
- IF — In-furrow surface
- PPI — Pre-plant incorporation of herbicide and antidote
- ST — Seed treatment

Herbicides
- EPTAM ® — S—ethyl N,N—dipropyl thiocarbamate
- VERNAM ® — S—propyl N,N—dipropyl thiocarbamate Injury Ratings:
- U = Antidotally untreated; % injury 4 weeks after herbicide application.
- T = Antidotally treated; % injury 4 weeks after treatment with herbicide plus antidote compound.
- ≃ = Indicates no change.

All rates shown are in pounds per acre.

TABLE IV

Antidotal Effectiveness

| Antidote | | | Herbicide | | % Crop Injury | | | | | | | | | | | | |
|---|---|---|---|---|---|---|---|---|---|---|---|---|---|---|---|---|---|
| | | | | | Milo | | Wheat | | Cotton | | Rice | | Barley | | Corn | | Soybean |
| Cmpd. No. | Rate | Method | Name | Rate | U | T | U | T | U | T | U | T | U | T | U | T | U | T |
| 1 | 5.00 | PPI | EPTAM | 0.50 | 94 | 60 | 85 | — | | | 45 | — | 70 | 60 | | | | |
|   | 5.00 | PPI | EPTAM | 5.00 | | | | | 94 | 50 | | | | | 95 | — | 60 | — |
| 2 | 5.00 | PPI | EPTAM | 0.50 | 94 | 30 | 85 | 70 | | | 45 | 10 | 70 | 40 | | | | |
|   | 5.00 | PPI | EPTAM | 5.00 | | | | | 95 | 50 | | | | | 95 | 10 | 60 | — |
|   | 0.50 | PPI | EPTAM | 5.00 | | | | | | | | | | | 95 | — | | |
|   | 0.05% | ST | EPTAM | 0.50 | | | | | 75 | 90 | | | | | | | | |
|   | 1.00 | PPI | EPTAM | 0.50 | | | | | 95 | — | | | | | | | | |
|   | 5.00 | PPI | EPTAM | 0.50 | | | | | 95 | — | | | | | | | | |
| 3 | 5.00 | PPI | EPTAM | 0.50 | 94 | — | 85 | — | | | 45 | — | 70 | 60 | | | | |
|   | 5.00 | PPI | EPTAM | 5.00 | | | | | 94 | 50 | | | | | 95 | — | 60 | — |
|   | 0.05% | ST | EPTAM | 5.00 | | | | | 90 | — | | | | | | | | |
|   | 1.00 | PPI | EPTAM | 5.00 | | | | | 93 | — | | | | | | | | |
|   | 5.00 | PPI | EPTAM | 5.00 | | | | | 93 | — | | | | | | | | |
| 4 | 5.00 | PPI | EPTAM | 0.50 | 94 | 30 | 85 | 70 | | | 45 | 10 | 70 | 40 | | | | |
|   | 5.00 | PPI | EPTAM | 5.00 | | | | | 94 | 50 | | | | | 95 | 10 | 60 | — |
|   | 0.05 | PPI | EPTAM | 5.00 | | | | | | | | | | | 95 | — | | |
|   | 1.00 | PPI | EPTAM | 0.50 | | | | | | | | | 98 | — | | | | |
|   | 5.00 | PPI | EPTAM | 0.50 | | | | | | | | | 98 | — | | | | |
|   | 0.5% | ST | EPTAM | 0.50 | | | | | | | | | 98 | 100 | | | | |
|   | 0.5% | ST | EPTAM | 0.50 | 98 | 100 | | | | | 75 | 95 | | | | | | |
|   | 1.00 | PPI | EPTAM | 0.50 | 95 | 98 | | | | | 95 | — | | | | | | |
|   | 5.00 | PPI | EPTAM | 0.50 | 95 | 100 | | | | | 95 | — | | | | | | |
| 5 | 5.00 | PPI | EPTAM | 0.50 | 94 | 30 | 85 | — | | | 45 | — | 70 | 50 | | | | |
|   | 5.00 | PPI | EPTAM | 5.00 | | | | | 94 | 50 | | | | | 95 | 0 | 60 | 100 |
|   | 0.05 | PPI | EPTAM | 5.00 | | | | | | | | | | | 95 | — | | |
| 6 | 5.00 | PPI | EPTAM | 0.50 | 94 | 60 | 85 | — | | | 45 | — | 70 | 40 | | | | |
|   | 5.00 | PPI | EPTAM | 5.00 | | | | | 94 | 60 | | | | | 95 | — | 60 | 50 |
| 7 | 5.00 | PPI | EPTAM | 0.50 | 94 | 10 | 85 | 0 | | | 45 | 10 | 70 | 0 | | | | |
|   | 5.00 | PPI | EPTAM | 5.00 | | | | | 94 | 40 | | | | | 95 | 20 | 60 | — |
|   | 0.5% | ST | EPTAM | 5.00 | | | | | 90 | — | | | | | | | | |
|   | 1.00 | PPI | EPTAM | 5.00 | | | | | 93 | 90 | | | | | | | | |
|   | 5.00 | PPI | EPTAM | 5.00 | | | | | 93 | — | | | | | | | | |
|   | 0.5% | ST | EPTAM | 0.50 | 98 | 100 | | | | | 75 | 80 | | | | | | |
|   | 1.00 | PPI | EPTAM | 0.50 | 95 | 100 | | | | | 95 | 80 | | | | | | |
|   | 5.00 | PPI | EPTAM | 0.50 | 95 | 100 | | | | | 95 | 60 | | | | | | |
|   | 1.00 | IF | VERNAM | 1.00 | | | | | | | | | | | 60 | — | | |
|   | 5.00 | IF | VERNAM | 1.00 | | | | | | | | | | | 60 | 100 | | |
| 8 | 5.00 | PPI | EPTAM | 0.50 | 94 | 40 | 85 | — | | | 45 | — | 70 | 40 | | | | |
|   | 5.00 | PPI | EPTAM | 5.00 | | | | | 94 | 60 | | | | | 95 | 80 | 60 | — |
| 9 | 5.00 | PPI | EPTAM | 0.50 | 94 | 50 | 85 | — | | | 45 | — | 70 | 60 | | | | |
|   | 5.00 | PPI | EPTAM | 5.00 | | | | | 94 | 40 | | | | | 95 | — | 60 | 40 |
|   | 0.5% | ST | EPTAM | 5.00 | | | | | 90 | — | | | | | | | | |
|   | 1.00 | PPI | EPTAM | 5.00 | | | | | 93 | 80 | | | | | | | | |
|   | 5.00 | PPI | EPTAM | 5.00 | | | | | 93 | 80 | | | | | | | | |
| 10 | 5.00 | PPI | EPTAM | 0.50 | 94 | 30 | 85 | — | | | 45 | — | 70 | 30 | | | | |
|   | 5.00 | PPI | EPTAM | 5.00 | | | | | 94 | 30 | | | | | 95 | — | 60 | — |
|   | 0.5% | ST | EPTAM | 5.00 | | | | | 90 | 60 | | | | | | | | |

TABLE IV-continued

| | Antidote | | Herbicide | | Antidotal Effectiveness % Crop Injury | | | | | | | | | | | | |
|---|---|---|---|---|---|---|---|---|---|---|---|---|---|---|---|---|---|
| | | | | | Milo | | Wheat | | Cotton | | Rice | | Barley | | Corn | | Soybean |
| Cmpd. No. | Rate | Method | Name | Rate | U | T | U | T | U | T | U | T | U | T | U | T | U | T |
| | 1.00 | PPI | EPTAM | 5.00 | | | | | 93 | — | | | | | | | | |
| | 5.00 | PPI | EPTAM | 5.00 | | | | | 93 | — | | | | | | | | |

TABLE V

| | Antidote | | Herbicide | | Herbicidal Effectiveness % Weed Injury | | | | | |
|---|---|---|---|---|---|---|---|---|---|---|
| | | | | | Water-grass | | Foxtail | | Wild Oat | |
| Cmpd. No. | Rate | Method | Name | Rate | U | T | U | T | U | T |
| 1 | 5.00 | PPI | EPTAM | 0.50 | | | 85 | — | 99 | — |
| 2 | 5.00 | PPI | EPTAM | 0.50 | | | 85 | 40 | 99 | 20 |
| | 0.05 | PPI | EPTAM | 5.00 | | | 98 | — | | |
| 3 | 5.00 | PPI | EPTAM | 0.50 | | | 85 | — | 99 | — |
| | 1.00 | PPI | EPTAM | 5.00 | | | 95 | — | | |
| | 5.00 | PPI | EPTAM | 5.00 | | | 95 | — | | |
| 4 | 5.00 | PPI | EPTAM | 0.50 | | | 85 | 40 | 99 | 20 |
| | 0.05 | PPI | EPTAM | 5.00 | | | 98 | — | | |
| 5 | 5.00 | PPI | EPTAM | 0.50 | | | 85 | — | 99 | — |
| | 0.05 | PPI | EPTAM | 5.00 | | | | | 98 | — |
| 6 | 5.00 | PPI | EPTAM | 0.50 | | | 85 | — | 99 | — |
| 7 | 5.00 | PPI | EPTAM | 0.50 | | | 85 | 30 | 99 | 10 |
| | 1.00 | PPI | EPTAM | 5.00 | | | 95 | — | 95 | — |
| | 5.00 | PPI | EPTAM | 5.00 | | | 95 | — | 95 | — |
| | 1.00 | IF | VERNAM | 1.00 | 70 | — | | | 95 | — |
| | 5.00 | IF | VERNAM | 5.00 | 70 | 100 | | | 95 | 100 |
| 8 | 5.00 | PPI | EPTAM | 0.50 | | | 85 | — | 99 | — |
| 9 | 5.00 | PPI | EPTAM | 0.50 | | | 85 | — | 99 | — |
| | 1.00 | PPI | EPTAM | 5.00 | | | 95 | — | | |
| | 5.00 | PPI | EPTAM | 5.00 | | | 95 | — | | |
| 10 | 5.00 | PPI | EPTAM | 0.50 | | | 85 | — | 99 | — |
| | 1.00 | PPI | EPTAM | 5.00 | | | | | 95 | — |
| | 5.00 | PPI | EPTAM | 5.00 | | | | | 95 | — |

FORMULATIONS

The object of the formulation is to apply the compositions to the locus where control is desired by a convenient method. The "locus" may include soil, seeds, seedlings, and vegetation.

The amount of antidote compound which comprises part of a herbicidal composition will generally range from approximately 0.001 to 30 parts by weight per weight of the herbicidal compound.

Formulations will generally contain several additives. Among these are inert ingredients, diluent carriers, organic solvents, water, oil and water, water in oil emulsions, carriers of dusts and granules, and surface active wetting, dispersing, and emulsifying agents.

Fertilizers, e.g., ammonium nitrate, urea and superphosphate, may also be included.

Aids to rooting and growth, e.g., compost, manure, humus, sand, etc., may likewise be included.

The formulations are commonly dusts, wettable powders, granules, solutions or emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anticaking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols; in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the herbicidal composition impregnated on a particulate inert carrier having a particle size of about 1 to 2 millimeters (mm) in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

I claim:
1. A composition comprised of
 (a) an antidotally effective amount of a compound of the formula

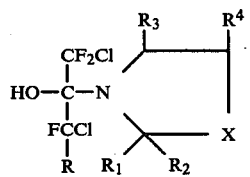

in which
R is selected from the group consisting of chloro and fluoro;
$R_1$–$R_4$ are each independently selected from the group consisting of hydrogen and 1–4 carbon alkyl; and
X is sulfur; and
(b) an herbicidally effective amount of a thiocarbamate of the formula

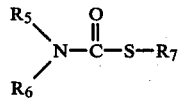

in which
$R_5$ is selected from the group consisting of 1–6 carbon alkyl and 2–6 carbon alkenyl;
$R_6$ is selected from the group consisting of 1–6 carbon alkyl, 2–6 carbon alkenyl, cyclohexyl and phenyl; or
$R_5$ and $R_6$ together form a hexamethylene group; and
$R_7$ is selected from the group consisting of 1–6 carbon alkyl, 1–6 carbon haloalkyl, 5–10 carbon alkylene ring, phenyl, substituted phenyl, wherein the substituents are 1–4 carbon alkyl, 1–4 carbon haloalkyl, and halo, benzyl and substituted benzyl, wherein the substituents are 1–4 carbon alkyl, 1–4 carbon haloalkyl, and halo.

2. A composition according to claim 1 in which $R_5$ and $R_6$ are each propyl and $R_7$ is ethyl.

3. A composition according to claim 2 in which R is chloro, $R_1$ and $R_2$ are each methyl, $R_3$ and $R_4$ are each hydrogen, and X is sulfur.

4. A method of reducing herbicidal crop injury caused by thiocarbamate herbicides which comprises adding to the soil a non-phytotoxic antidotally effective amount of a compound of the formula

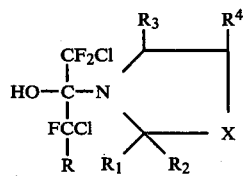

in which
R is selected from the group consisting of chloro and fluoro;
$R_1$–$R_4$ are each independently selected from the group consisting of hydrogen and 1–4 carbon alkyl; and
X is sulfur.

5. A method according to claim 4 in which R is chloro, $R_1$ and $R_2$ are each methyl, $R_3$ and $R_4$ are each hydrogen, and X is sulfur.

* * * * *